US00PP33151P2

(12) United States Plant Patent
de Groot

(10) Patent No.: US PP33,151 P2
(45) Date of Patent: Jun. 15, 2021

(54) ***ROSA* PLANT NAMED 'RUIBG0025A'**

(50) Latin Name: *Rosa hybrida*
Varietal Denomination: RUIBG0025A

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 16/987,167

(22) Filed: Aug. 6, 2020

(51) Int. Cl.
*A01H 5/02* (2018.01)
*A01H 6/74* (2018.01)

(52) U.S. Cl.
USPC ..... Plt./103
CPC ..... *A01H 6/749* (2018.05)

(58) Field of Classification Search
USPC ..... Plt./103
CPC ..... A01H 5/02
See application file for complete search history.

*Primary Examiner* — Kent L Bell
(74) *Attorney, Agent, or Firm* — Cassandra Bright

(57) ABSTRACT

A new and distinct hybrid *Rosa* cultivar named 'RUIBG0025A' is disclosed, characterized by pure white flowers on highly floriferous, low-growing, dense plants. The new variety is a multiflora landscape type garden rose.

2 Drawing Sheets

Figure 1:
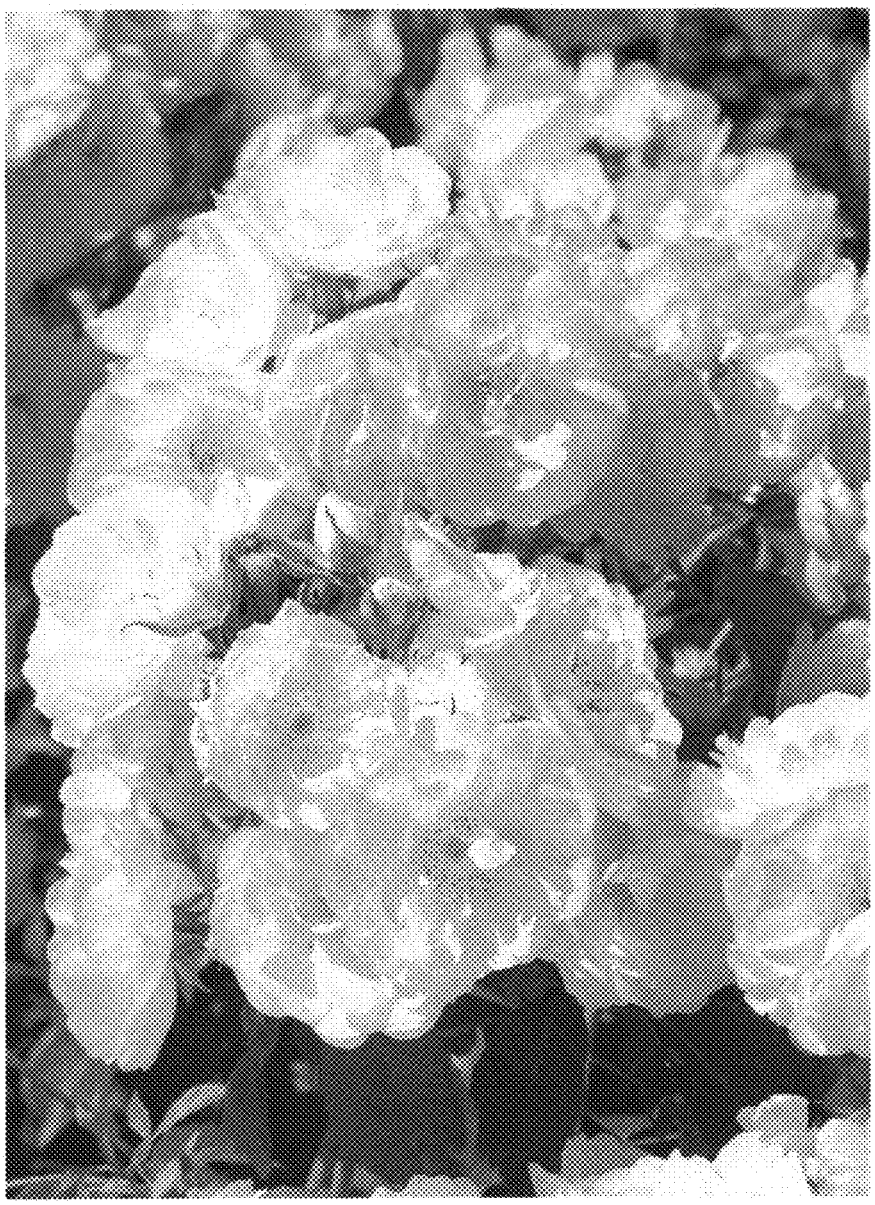

Latin name of the genus and species: *Rosa hybrida.*
Variety denomination: 'RUIBG0025A'.

BACKGROUND OF THE INVENTION

The new *Rosa* cultivar is a product of a planned breeding program conducted by the inventor. The cross resulting in this new variety was made in May 2006 at a nursery in Hazerswoude, the Netherlands.

The seed parent is the unpatented variety *Rosa* 'RUIRC0106A'. The pollen parent is the unpatented variety *Rosa* 'RUIBA028B'. The new variety was selected in May 2009 by the inventor at the same nursery in Hazerswoude, the Netherlands. The inventor continued observing characteristics of the new variety for several years, in the controlled conditions of the research nursery.

Asexual reproduction of the new cultivar was performed by vegetative softwood cuttings. This was first performed at a greenhouse in Hazerswoude, the Netherlands, in May 2009, and has shown that the unique features of this cultivar are stable and reproduced true to type in successive generations.

SUMMARY OF THE INVENTION

The cultivar 'RUIBG0025A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIBG0025A' These characteristics in combination distinguish 'RUIBG0025A' as a new and distinct *Rosa* cultivar:

1. Pure white flowers.
2. Highly floriferous plants.
3. Low-growing, dense plants.
4. Suitability for landscape and groundcover use.

5. Flowering continuously from June until September in the Netherlands.

PARENTAL COMPARISON

Plants of the new cultivar 'RUIBG0025A' are similar to plants of the seed parent, in most horticultural characteristics, however, plants of the new cultivar 'RUIBG0025A' differ in the following:

1. Foliage of the new variety is darker green and less dense than foliage of the seed parent.

Plants of the new cultivar 'RUIBG0025A' are similar to plants of the pollen parent in most horticultural characteristics, however, plants of the new cultivar 'RUIBG0025A' differs in the following;

1. New variety has white flowers, while the pollen parent has pink flowers.

COMMERCIAL COMPARISON

Plants of the new cultivar 'RUIBG0025A' can be compared to the commercial variety *Rosa* 'Flower Carpet White', U.S. Plant Pat. No. 9,573. These varieties are similar in most horticultural characteristics, however 'RUIBG0025A' differs in the following:

1. The new variety produces flowers with a larger diameter.
2. The new variety produces more flowers per inflorescence.

Plants of the new cultivar 'RUIBG0025A' can be compared to the unpatented commercial variety *Rosa* 'Wedding Dress'. These varieties are similar in most horticultural characteristics, however 'RUIBG0025A' differs in the following:

1. Flowers of the new variety are pure white, flowers of this comparator are white with a pink undertone.

2. Flowers of the new variety have a smaller center and lighter stamens than flowers of this comparator, which have an open center and dark stamens.

BRIEF DESCRIPTION OF THE PHOTOGRAPHS

The accompanying photograph in FIG. 1 illustrates a close-up view of a typical inflorescence.

Figure 2:
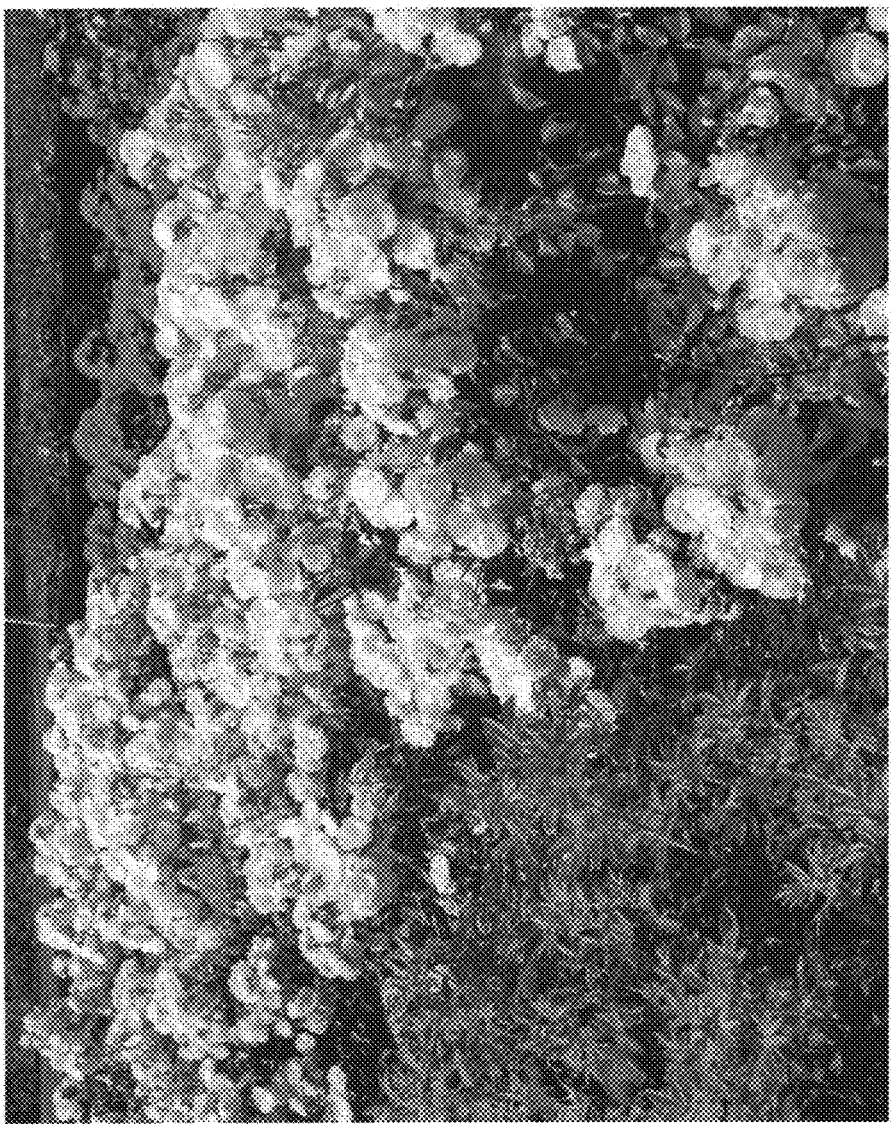

FIG. 2 illustrates in full color typical plants of 'RUIBG0025A' grown in the ground at a nursery in De Kwakel, the Netherlands. Plants in FIG. 2 are approximately 2 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIBG0025A' plants grown outdoors, in De Kwakel, the Netherlands. The growing temperature ranged from approximately 20° C. to 26° C. during the day and from approximately 16° C. to 18° C. during the night. Measurements were taken in August. General light conditions were very bright, normal sunlight. Measurements and numerical values represent averages of typical plant types.

Botanical classification: *Rosa* 'RUIBG0025A'.

Market classification: Landscape/groundcover multiflora.

PROPAGATION

Time to initiate roots: 10 days at approximately 25° C.

Time to produce a rooted cutting: 21 days at approximately 25° C.

Typical method: Vegetative terminal cuttings, does not require grafting.

PLANT

Growth habit: Intermediate.

Age of plant described: 2 years.

In a container or in the ground: Ground.

Height: 65 cm.

Plant spread: 55 cm.

Rootstock: Own roots.

Branching characteristics:

Length of primary lateral branches: Approximately 26 cm.

Diameter of lateral branches: Approximately 1 cm.

Quantity of lateral branches: 4 to 8 main laterals.

Branching arrangement: Compound.

Branches-young wood:

*Diameter*.—Approximately 0.4 cm.

*Texture*.—Smooth.

*Approximate density/quantity of thorns*.—Sparse.

*Color*.—Near RHS Yellow-Green 146C.

Branches-old wood:

*Diameter*.—Approximately 0.7 cm, after 0.5 years.

*Color*.—Near RHS Yellow-Green 146B.

*Texture*.—Smooth.

*Approximate density/quantity of thorns*.—Sparse, 2 to 3 per 5 cm linear stem.

*Thorns*.—Color: Near RHS Greyed-Red 178A. Height: 0.9 cm. Diameter: 0.6 cm. Shape: Deltoid.

FOLIAGE

Leaf:

*Arrangement*.—Imparipinnate.

*Quantity*.—Approximately 5 per main branch.

*Average length*.—Approximately 13 cm.

*Average width*.—Approximately 10 cm.

Leaflet:

*Quantity*.—3, 5, or 7 per leaf.

*Average length*.—Approximately 4.5 cm.

*Average width*.—Approximately 3 cm.

*Shape of blade*.—Ovate.

*Apex*.—Apiculate.

*Base*.—Obtuse.

*Margin*.—Serrate.

*Texture of top surface*.—Smooth.

*Texture of bottom surface*.—Smooth.

*Pubescence*.—Puberulous.

*Leaf internode length*.—6-8 cm.

*Color*.—Young foliage upper side: Near RHS Green 137D. Young foliage under side: Near RHS Yellow-Green 147C. Mature foliage upper side: Near RHS Green NN137A. Mature foliage under side: Near RHS Yellow-Green 147B.

*Venation*.—Type: Pinnate. Venation color upper side: RHS Yellow-Green 144B. Venation color under side: RHS Yellow-Green 144C.

Stipule:

*Quantity*.—1.

*Length*.—1.7 cm.

*Width*.—0.4 cm.

*Shape*.—Narrow deltoid to oblong.

*Margin*.—Deeply serrate.

*Base*.—Truncate.

*Color*.—RHS Yellow-Green N144B.

*Texture*.—Smooth.

Petiole:

*Length*.—2 cm.

*Width*.—0.2 cm.

*Color*.—Near RHS Green 137D.

*Texture*.—Hairy.

Petiolule:

*Length*.—1 to 2 mm.

*Width*.—1 mm.

*Color*.—Near RHS Greyed-Red 180C.

*Texture*.—Slightly pubescent.

Rachis:

*Length*.—2 cm.

*Width*.—0.2 cm.

*Color*.—Near RHS Green 137D.

*Texture*.—Pubescent.

FLOWER

Natural flowering season: June-September in Europe.

Begins flowering after how many years/months: 3 months.

Inflorescence type: Multiflora.

Rate of flower opening: Approximately 5 days from bud to fully opened flower.

Flower longevity on plant: 6 days, after fully opened.

Quantity of flowers: 10 flowers per inflorescence.

Inflorescence size:
*Diameter*.—Approximately 9 cm.
*Depth*.—Approximately 6 cm.
Peduncle:
*Length*.—5 cm.
*Diameter*.—0.25 cm.
*Texture*.—Glabrous to very slightly hirsute.
*Color*.—Near RHS Green 138B.
Petals:
*Petal arrangement*.—Loose.
*Length*.—2.4 cm.
*Width*.—2 cm.
*Shape*.—Obcordate.
*Margin*.—Entire.
*Apex*.—Retuse.
*Base*.—Acute.
*Petal quantity*.—25.
*Texture*.—Velvety upper and lower surfaces.
*Color*.—When opening: Upper surface: Near RHS White NN155D. Lower surface: Near RHS White N155C. Fully opened: Upper surface: Near RHS White NN155D. Lower surface: Near RHS White NN155D. Color Changes when aging: No.
Bud:
*Shape*.—Ovate.
*Length*.—Approximately 1.7 cm.
*Diameter*.—Approximately 1 cm.
*Color*.—Near RHS White N155C.
Sepals:
*Quantity*.—5.
*Length*.—1.7 cm.
*Width*.—0.8 cm.
*Apex*.—Acuminate, twisting.
*Margin*.—Entire.
*Shape*.—Lanceolate.
*Color*.—Interior Surface: Near RHS Green 137D. Exterior Surface: Near RHS Green 137C.
*Texture*.—Velvet.
Receptacle:
*Length*.—0.8 cm.
*Width*.—0.4 cm.
*Shape*.—Oblong.
*Color*.—Near RHS Yellow-Green 144D.
Fragrance: None.

REPRODUCTIVE ORGANS

Stamens:
*Quantity*.—Average 40.
*Filament length*.—Average 0.8 cm.
*Filament color*.—Near RHS Yellow-Orange 18D.
Anthers:
*Length*.—12 mm.
*Shape*.—Oblong.
*Color*.—RHS Greyed-Orange 163B.
*Pollen*.—Color: Near RHS Greyed-Orange 163D. Quantity: Sparse.
Pistil:
*Number*.—15.
*Length*.—3 mm.
*Style*.—Length: Approximately 0.2 cm. Color: Near RHS Greyed-Orange 163A.
Stigma:
*Shape*.—Round.
*Color*.—Near RHS Greyed-Orange 163D.

OTHER CHARACTERISTICS

Seeds and fruits: Not observed.
Disease/pest resistance: Neither resistance nor susceptibility to typical diseases and pests of landscape roses observed.
Temperature tolerance: USDA zones 4-9.

What is claimed is:

1. A new and distinct hybrid cultivar of *Rosa* multiflora landscape type plant named 'RUIBG0025A' as herein illustrated and described.

* * * * *